United States Patent [19]

Zanker

[11] 4,162,263

[45] Jul. 24, 1979

[54] MANUFACTURE OF ALIPHATIC OR CYCLOALIPHATIC ISOCYANATES

[75] Inventor: Fritz Zanker, Worms, Fed. Rep. of Germany

[73] Assignee: BASF Aktiengesellschaft, Fed. Rep. of Germany

[21] Appl. No.: 867,145

[22] Filed: Jan. 5, 1978

[30] Foreign Application Priority Data

Jan. 27, 1977 [DE] Fed. Rep. of Germany ....... 2703281

[51] Int. Cl.$^2$ .......................................... C07C 118/00
[52] U.S. Cl. .................................................. 260/453 P
[58] Field of Search ..................................... 260/453 P

[56] References Cited

U.S. PATENT DOCUMENTS

| | | | |
|---|---|---|---|
| 3,388,145 | 6/1968 | Merz | 260/453 P |
| 3,969,389 | 7/1976 | Urbach et al. | 260/453 P |
| 3,991,094 | 11/1976 | Zanker | 260/453 P |
| 4,082,787 | 4/1978 | Bassett et al. | 260/453 P |

*Primary Examiner*—Dolph H. Torrence
*Attorney, Agent, or Firm*—Keil & Witherspoon

[57] ABSTRACT

Aliphatic and cycloaliphatic isocyanates are manufactured by thermal decomposition of aliphatic or cycloaliphatic carbamic acid chlorides in the presence of an inert organic solvent of lower boiling point than that of the isocyanate formed. The decomposition is carried out in a reaction vessel surmounted by a rectifying unit, which in turn is surmounted by a reflux condenser, the isocyanate formed being condensed in the rectifying unit at a temperature above the boiling point of the solvent.

4 Claims, No Drawings

MANUFACTURE OF ALIPHATIC OR CYCLOALIPHATIC ISOCYANATES

The present invention relates to a process for the manufacture of aliphatic or cycloaliphatic isocyanates by thermal decomposition of aliphatic or cycloaliphatic carbamic acid halides in the presence of an inert organic solvent which has a lower boiling point than that of the resulting isocyanate.

The manufacture of isocyanates by thermal decomposition of carbamic acid halides in the presence of inert organic solvents has been disclosed. The reaction can be represented by the following equation:

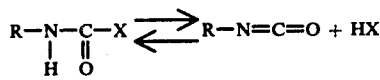

To prevent the reverse reaction occurring, the hydrogen halide must be removed from the equilibrium.

If the decomposition is carried out in the presence of organic bases, eg. tertiary amines or N,N-dialkylcarboxylic acid amides (German Laid-Open Application DOS No. 1,593,554) or in the presence of aqueous solutions or suspensions of acid acceptors, eg. alkali metal hydroxides and alkaline earth metal hydroxides, alkali metal carbonates and alkaline earth metal carbonates, alkali metal bicarbonates, trialkylamines, pyridine and N-methylpiperidine (British Pat. No. 1,208,862), the hydrogen halide formed during the reaction can be bonded chemically.

The above processes have the disadvantage that the isocyanate are formed in a medium in which they are prone to decompose. Houben-Weyl, Methoden der organischen Chemie, volume 8, page 136 (1952), Georg-Thieme-Verlag, Stuttgart, discloses that isocyanates dimerize in the presence of tertiary amines. They are extremely unstable to aqueous alkali and are substantially converted to carbamates or carbamic acids even if stoichiometric amounts of aqueous alkali are used.

Annalen, 562 (1949), 75–109 discloses the thermal decomposition of N-phenyl-carbamic acid chloride and points out that the isocyanates can only be isolated if the hydrogen chloride formed is bonded by means of chemical agents, eg. calcium oxide. In this process, side reactions, eg. the formation of polymeric isocyanates, occasionally occur. Furthermore, the decomposition is stated to lead to isocyanates only in the case of aromatic carbamic acid chlorides but not in the case of aliphatic carbamic acid chlorides.

German Pat. No. 1,193,034 discloses a process in which the isocyanate formed on thermal decomposition of alkylcarbamic acid chlorides is distilled off through a column and the hydrogen chloride is at the same time removed from the reaction chamber through a separate reflux condenser.

A process has also been disclosed, in German Laid-Open Application DOS No. 2,411,442, which is based on removing the hydrogen halide, formed on decomposition of the alkylcarbamic acid halides, from the reaction mixture by passing an inert gas through the latter. Solvent, isocyanate or carbamic acid halide entrained by the inert gas can be washed out, for example with solvents, and be resubjected to thermal decomposition.

The thermal decomposition of alkylcarbamic acid halides can also be carried out in two stages, by effecting a partial decomposition in the first reaction vessel and completing the decomposition in the second reaction vessel whilst passing an inert gas through the mixture. The inert gas is subsequently purified by recombining the hydrogen halide with isocyanate and is recycled to the second reaction vessel. The carbamic acid chloride formed in this purification step can be recycled to the first reaction vessel and be thermally decomposed therein (German Laid-Open Application DOS No. 2,503,270).

I have found that an isocyanate of the formula

where R is an aliphatic radical of 1 to 10 carbon atoms or a cycloaliphatic radical of 5 to 12 carbon atoms may be obtained by thermal decomposition of an aliphatic or cycloaliphatic carbamic acid halide of the formula

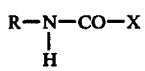

where R has the above meaning and X is halogen, in the presence of an inert organic solvent, if the thermal decomposition of the carbamic acid halide is carried out in the presence of an inert organic solvent which has a lower boiling point that that of the resulting isocyanate, in a reaction vessel surmounted by a rectifying unit which is in turn surmounted by a reflux condenser, under reflux conditions, the resulting isocyanate is condensed in the rectifying unit at a temperature above the boiling point of the solvent at the prevailing pressure, the hydrogen halide formed during the decomposition is removed through the reflux condenser and the solvent is condensed in the reflux condenser.

In contrast to the processes disclosed in German Pat. No. 1,193,034 and German Laid-Open Applications DOS No. 2,411,442 and DOS No. 2,503,270, in which the recombination of the split-off hydrogen halide with the isocyanate which condenses in the reflux condenser is prevented by removing the hydrogen halide through a separate reflux condenser or by expelling the hydrogen halide from the reaction chamber by passing an inert gas through it, the recombination to form the carbamic acid chloride is prevented, in the process according to the invention, by only condensing the solvent, which is lower-boiling than the isocyanate, on the cold surface of the reflux condenser.

Compared to the conventional process, the process according to the invention can be carried out with less expensive apparatus, and with lower production costs.

Starting materials II and, accordingly, end products I are those where R is an aliphatic radical of 1 to 10 carbon atoms or a cycloaliphatic radical of 5 to 12 carbon atoms amongst which branched or unbranched alkyl of 1 to 10, preferably 1 to 4, especially 1 to 3, carbon atoms, branched or unbranched alkenyl or branched or unbranched alkynyl, each of 2 to 6, especially 2 or 3, carbon atoms, and unsubstituted or alkyl-substituted, especially methyl-substituted, cycloalkyl of 5 to 12 carbon atoms are preferred. In the formula of the carbamic acid chlorides and the isocyanates, X is halogen, eg. chlorine or bromine, especially chlorine. The alkyl, alkenyl and alkynyl radicals may also be substituted by groups and/or atoms which are inert under the reaction conditions, eg. alkyl, alkoxy or alkylmercapte each of 1 to 5 carbon atoms, or chlorine.

Examples of suitable starting compounds II are methyl-, ethyl-, n-propyl-, i-propyl-, n-butyl-, i-butyl-, sec.-butyl-, t-butyl-, 2-methylbutyl-1-, 3-methylbutyl-1-, 2-methylbutyl-2-, 3-methylbutyl-2-, pentyl-1-, pentyl-2-, pentyl-3-, neo-pentyl-, n-hexyl-, n-octyl-, allyl-, 3,3-dimethylallyl-3-, 3-methyl-3-ethyl-allyl-3-, but-1-ynyl-3-, 3-methyl-but-1-ynyl-3-, 3-methyl-pent-1-ynyl-3-, 2-methoxyethyl-, 2-ethoxyethyl-, 3-methoxypropyl-, 3-ethoxypropyl, 1-methoxy-butyl-2-, 1-n-propoxy-propyl-2-, methoxy-t-butyl-, ethoxy-t-butyl, methylmercaptopropyl-, ethylmercaptopropyl-, α,α-bis-chloromethylethyl, α,α-dimethyl-β-chloroethyl, cyclopentyl-, cyclohexyl-, cyclooctyl-, 2-methylcyclohexyl-, 4-methylcyclohexyl- and cyclododecyl-carbamic acid chloride and corresponding carbamic acid bromides. Methyl-, ethyl-, n-propyl- and isopropyl-carbamic acid chloride are preferred.

The decomposition is in general carried out at from 30° to 180° C., preferably from 35° to 130° C., advantageously under reflux at the boiling point of the solvent at the prevailing pressure and under the autogenous pressure of the decomposition mixture of starting material II and solvent.

The solvents used are organic solvents which are inert under the reaction conditions and have a boiling point lower than that of the resulting isocyanate, and especially solvents which readily dissolve the starting material II but only dissolve the hydrogen halide slightly, if at all. Examples of suitable solvents are aliphatic and cycloaliphatic hydrocarbons, eg. propane, n-butane, i-butane, n-pentane and its isomers, n-hexane and its isomers, cyclopentane, methylcyclopentane, cyclohexane and methylcyclohexane; aliphatic halohydrocarbons, eg. methyl chloride, methylene chloride, chloroform, carbon tetrachloride, ethyl chloride, ethylene chloride, n-propyl chloride, i-propyl chloride, n-butyl chloride and its isomers, ethylidene chloride, dichloroethane and fluorinated or partially fluorinated compounds, eg. 1,1,1-trifluoro-2,2-dichlorethane, 1,1,2-trifluoro-1,2-dichloroethane, and 1-fluoro-1,1-dichloroethane; aromatic hydrocarbons and chlorohydrocarbons, benzene, toluene, xylene and chlorobenzene, esters, eg. methyl formate, ethyl acetate and methyl propionate, ethers, eg. dimethyl ether and diethyl ether, cyclic ethers, eg. tetrahydrofuran, and other organic compounds, eg. carbon disulfide and acetonitrile, as well as mixtures of these solvents.

According to the invention, during the thermal decomposition of the carbamic acid halide the solvent is condensed on the cold surfaces of the condenser, whilst the isocyanate formed has already been completely condensed on the warmer surfaces of the separating device, in accordance with the separating action of the latter and the higher boiling point of the isocyanate. In this way, the isocyanate formed is prevented from recombining, on the cold surfaces of the condenser, with the hydrogen halide eliminated from the carbamic acid halide, to form carbamic acid halide. The solvent condensed on the cold surfaces of the condenser, which is a poor solvent for hydrogen halide, allows the eliminated hydrogen halide to pass.

The amount of solvent is advantageously from 40 to 3,000 percent by weight, preferably from 80 to 900 percent by weight, based on starting material II.

In the extreme case, the amount of solvent need only be sufficiently large to prevent contact of the particular isocyanate with the cold walls of the condenser.

It is advantageous to add to the decomposition mixture a second solvent which has a higher boiling point than that of the particular isocyanate, in order to prevent polymerization of the isocyanate when the latter is worked up by distillation, through avoiding the isocyanate becoming too highly concentrated. Suitable second solvents are inert solvents which dissolve hydrogen halide only slightly, if at all, eg. toluene, xylene, chlorobenzene and dichlorobenzene.

When a second solvent is added, the amount of solvent is nevertheless, in total, from 40 to 3,000 percent by weight, preferably from 80 to 900 percent by weight, based on starting material II.

The process of the invention may be carried out continuously or batchwise, under atmospheric or superatmospheric pressure.

Advantageously, it is carried out as follows:

The carbamic acid halide, the solvent which is lower-boiling than the resulting isocyanate, and, where such is used, the solvent which is higher-boiling than the resulting isocyanate, are introduced into a decomposition vessel surmounted by a rectifying unit which in turn is surmounted by a reflux condenser. The mixture is refluxed, whilst removing the eliminated hydrogen halide through the reflux condenser. If the elimination of hydrogen halide is incomplete because the temperature is too low under atmospheric pressure, the boiling point is advantageously raised by carrying out the thermal decomposition under pressure, and the mixture is refluxed until the resulting hydrogen halide has been completely removed through the reflux condenser.

The isocyanate is advantageously isolated by distillation. Under certain circumstances, the reaction mixture containing the isocyanate may also be used directly for further chemical reactions.

The rectifying unit is advantageously a column fitted with rectifying trays, eg. sieve trays or bubble-cap trays, or filled with packings, eg. Raschig rings, or is a similarly fitted or packed tower.

The isocyanates which may be manufactured by the process of the invention are valuable starting materials for the manufacture of crop protection agents, pesticides, dyes, synthetic resins and plastics, water-repellent finishes for textiles, detergents, bleaching agents and adhesives. In particular, they are of value for conversion to urethanes, eg. for use as foams or high molecular weight, highly flexible coatings, or to ureas. Regarding their uses, reference may be made to the above publications and to Ullmanns Encyklopadie der technischen Chemie, volume 9, pages 11, 12 and 404 (1957) and volume 17, page 204 (1966).

EXAMPLE 1

The decomposition apparatus consists of a decomposition vessel, surmounted by a column which is about 70 cm high and is filled with Raschig rings, the column in turn being surmounted by a reflux condenser, cooled to about −15° C., with a downstream manometer and pressure-regulating valve.

200 parts by weight of ethylcarbamic acid chloride, 264 parts by weight of tert.-butyl chloride and 265 parts by weight of toluene are introduced into the decomposition vessel. The reaction mixture is then boiled for 2 hours under reflux, during which time the reflux temperature soon reaches 51° C. It is then raised to about 91° C. by increasing the autogenous pressure by 2.2 bars by means of the pressure-regulating valve in the hydrogen halide outlet downstream from the condenser.

After boiling for 5 hours under these reflux conditions, analysis of the material in the decomposition vessel indicates an ethyl isocyanate content of about 19.5% (theoretical content, 20%) and an ethylcarbamic acid chloride content of less than 0.2%.

EXAMPLE 2

210 parts by weight of isopropylcarbamic acid chloride mixed with 280 parts by weight of toluene and 280 parts by weight of n-hexane are decomposed in the apparatus and by the method described in Example 1, in the course of 6 hours at a reflux temperature of from 103° to 105° C. and under 3.2 bars pressure. After completion of the decomposition, the entire n-hexane and the isopropyl isocyanate formed are distilled conjointly from the apparatus under normal pressure until the toluene begins to boil. 410 parts by weight of distillate are obtained, containing, according to a determination by IR spectroscopy, 34% of isopropyl isocyanate, corresponding to a yield of about 95% of theory. Isopropylcarbamic acid chloride cannot be detected in the distillate by IR spectroscopy.

EXAMPLE 3

210 parts by weight of isopropylcarbamic acid chloride are added to a mixture of 280 parts by weight of n-pentane and 280 parts by weight of toluene in the decomposition apparatus described in Example 1. The mixture is then refluxed for 15 hours under atmospheric pressure. After 6 hours, the temperature is about 54° C. in the decomposition vessel and 36° on the reflux condenser and remains constant for the next 8 hours. IR analysis shows an isopropylcarbamic acid chloride content of less than 0.2%. Working up by distillation gives 141 parts of isopropyl isocyanate, corresponding to 96% of theory; boiling point 74° C.

If a similar method is used to decompose 134 parts by weight of n-butylcarbamic acid chloride in 392 parts by weight of ethylene chloride under atmospheric pressure and reflux conditions, elimination of hydrogen chloride is complete after 4 hours. The yield of n-butyl isocyanate is 95 parts by weight, corresponding to 97% of theory; boiling point 114°-116° C.

The decomposition of 161.5 parts by weight of cyclohexylcarbamic acid chloride in 500 parts by weight of toluene, carried out similarly under atmospheric pressure and reflux conditions, again gives cyclohexyl isocyanate free from carbamic acid chloride after a reaction time of 4 hours; yield, 120 parts by weight, corresponding to 95% of theory; boiling point 60°-62° under 14 mm Hg.

EXAMPLE 4

164 parts by weight of methylcarbamic acid chloride, 400 parts by weight of ethyl chloride and 500 parts by weight of toluene are decomposed in a stainless steel decomposition apparatus, consisting of a decomposition vessel surmounted by a column which is about 2 m high and is filled with stainless steel Raschig rings, and is in turn surmounted by a reflux condenser cooled to about −15° C., with a downstream manometer and pressure-regulating valve, the decomposition being carried out for 21 hours at a reflux temperature of 90°-93° C. under a pressure of 9.5-10 bars. After this time, elimination of hydrogen chloride is virtually complete. Working up by distillation gives 89 parts by weight of methyl isocyanate free from carbamic acid chloride, corresponding to 89% of theory; boiling point 38°-40° C.

I claim:

1. A process for the manufacture of an isocyanate of the formula

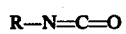

where R is an aliphatic radical of 1 to 10 carbon atoms or a cycloaliphatic radical of 5 to 12 carbon atoms, which comprises thermally decomposing an aliphatic or cycloaliphatic carbamic acid halide of the formula

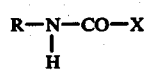

where R has the above meaning and X is halogen, in the presence of an inert organic solvent which has a lower boiling point than that of the resulting isocyanate, in a reaction vessel surmounted by a rectifying unit which is in turn surmounted by a reflux condenser, and under reflux conditions, condensing the resulting isocyanate in the rectifying unit at a temperature above the boiling point of the solvent at the prevailing pressure, removing the hydrogen halide formed during the decomposition through the reflux condenser and condensing the solvent in the reflux condenser.

2. A process of claim 1, wherein the thermal decomposition of the carbamic acid halide is carried out in the presence of a second inert organic solvent which has a higher boiling point than that of the resulting isocyanate.

3. A process of claim 1, wherein the thermal decomposition of the carbamic acid halide is carried out at from 30° to 180° C.

4. A process of claim 1, wherein, in the formula of the carbamic acid halide, R is alkyl of 1 to 4 carbon atoms and X is chlorine.